United States Patent [19]

Groves et al.

[11] 4,260,379
[45] Apr. 7, 1981

[54] ENDODONTIC INSTRUMENT

[75] Inventors: William A. Groves, Ann Arbor; Frank N. Lentine, Taylor, both of Mich.

[73] Assignee: Sybron Corporation, Rochester, N.Y.

[21] Appl. No.: 39,927

[22] Filed: May 17, 1979

[51] Int. Cl.³ ............................................. A61C 5/02
[52] U.S. Cl. ..................................... 433/102; 408/210
[58] Field of Search .................. 433/102, 81; 408/210

[56] References Cited

U.S. PATENT DOCUMENTS

| 1,067,015 | 7/1913 | Fowler | 433/102 |
| 1,307,446 | 6/1919 | Kerr | 433/102 |
| 2,504,601 | 4/1950 | Spry | 408/210 |
| 3,991,454 | 11/1976 | Wale | 408/210 |
| 4,019,254 | 4/1977 | Malmin | 433/102 |
| 4,028,810 | 6/1977 | Vice | 433/102 |

OTHER PUBLICATIONS

"Union Broach" add, Dental Survey, Jul. 1979, p. 19.

*Primary Examiner*—Gene Mancene
*Assistant Examiner*—John J. Wilson
*Attorney, Agent, or Firm*—Theodore B. Roessel; Roger Aceto

[57] ABSTRACT

An endodontic instrument formed by twisting a tapered blank which in cross section is ground to an oblique parallelogram, the obtuse angles of the oblique parallelogram cross section being between 105°–120°.

13 Claims, 5 Drawing Figures

FIG. 4

ENDODONTIC INSTRUMENT

BACKGROUND OF THE INVENTION

The present invention relates to an endodontic instrument and more particularly to an endodontic cutting instrument which is manually manipulated to clean and enlarge the root canals of teeth.

Generally there are three types of such instruments in use. First, there is an endodontic file or K-file which is substantially a square ground tapered rod which is axially twisted to form the instrument. Twisting provides the instrument with four spiral cutting edges. This instrument is generally considered to be the strongest of the three types and is used as a file wherein it is inserted into the root canal and axially reciprocated to remove pulp from the root canal.

The second type is substantially a triangular ground tapered rod. This rod, too, is twisted to form the instrument wherein twisting provides the instrument with three spiral cutting edges. This instrument is generally considered to be the best cutting instrument and is used primarily as a reamer wherein it is inserted into the root canal and twisted to ream or enlarge the canal.

The third type of instrument is a Hedstrom file. The Hedstrom file is a cylindrically tapered rod which is fluted by grinding along the taper in a helical pattern to form the finished instrument. The Hedstrom file is generally considered to be the weakest of the three instruments but it is also considered to have the best debris removal characteristics of the three types.

Each of these three types of instruments represents a compromise from an ideal instrument. For example, the K-file or square shaped instrument is strong, but has poorer cutting characteristics than the triangular shaped instrument and does not have the debris removal characteristics of the Hedstrom file. The reamer or triangular shaped instrument has good cutting characteristics, but is not as strong as the K-file and does not have the debris removal characteristics of the Hedstrom file. The Hedstrom file has the best debris removal characteristics of the three instruments and a cutting ability between the square and triangular, but is the weakest of the three instruments.

The endodontic instrument of the present invention, however, combines the best features of each of the three standard types and provides an instrument which is strong, has good cutting characteristics and good debris removal characteristics.

SUMMARY OF THE INVENTION

The endodontic instrument of the present invention may be characterized in one aspect, thereof by the file or reamer portion being manufactured by twisting an elongated tapered parallelogram ground bar. In other words, the bar in cross section is the shape of a parallelogram having two acute and two obtuse angles. This configuration when twisted provides a file with a major diameter approximately corresponding to the long diagonal of the parallelogram and a minor diameter corresponding generally to the short diagonal of the parallelogram. The spiral cutting edges formed when the bar is twisted extend only along the ends of the major diameter of the file.

DESCRIPTION OF THE PREFERRED EMBODIMENTS

Figures 1, 2:
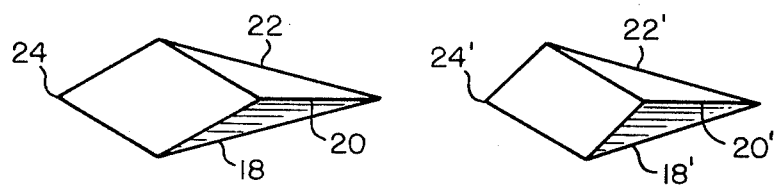
FIG. 1 is a prospective view showing a parallelogram ground axially tapering rod from which the endodontic instrument of the present invention is made.
FIG. 2 is a view similar to FIG. 1 showing a different configuration of the rod.
Figure 3:
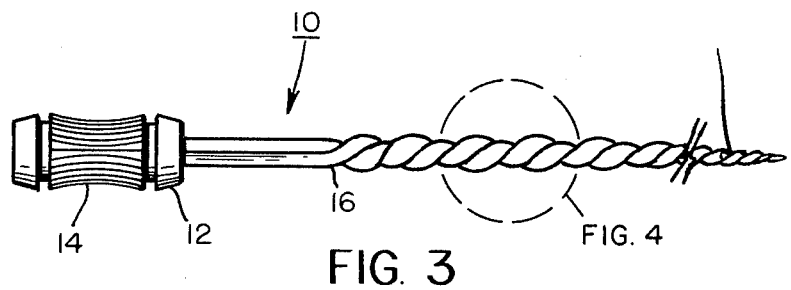
FIG. 3 is a side elevation view showing the finished endodontic instrument.

Referring to the drawings, FIG. 3 shows a complete endodontic instrument generally indicated at 10. The instrument includes a handle 12 which has a contoured portion 14 to facilitate the manipulation of the instrument between the thumb and forefinger of the user. Extending axially from the handle is the elongated tapered file or reamer 16. This file or reamer is made by grinding a elongated tapered rod to the shape of a parallelogram in cross section. This can be either a equilateral parallelogram i.e. a rhombus ground cross section having two acute and two obtuse angles as shown in FIG. 1, or a rhomboid ground cross section wherein only the opposite side of the parallelogram are equal. We have found that for best results, the acute angles of the parallelogram should be between about 60° to 75° and the obtuse angles between about 105° to 120°.

After the rod has been ground to the appropriately shaped cross section, the ground blank is axially twisted anywhere from 10 to 20 or more full turns. This provides the file with four spiraling edges corresponding to the blank edges 18, 20, 22 and 24. After the blank is twisted, it is attached to handle 12 by any suitable means well known in the art to provide the complete endodontic instrument.

Figure 4:
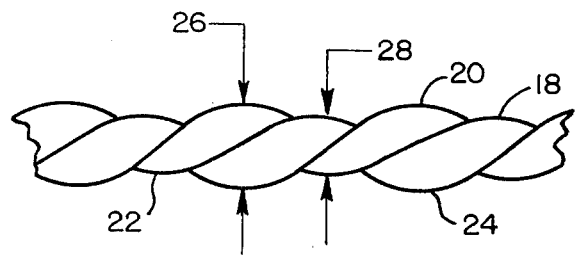
FIG. 4 is a view on an enlarged scale of a portion of the instrument shown in FIG. 3.
Figure 5:
FIG. 5 is a view similar to FIG. 4 only showing the prior art instrument.

The unique feature of the instrument of the present invention provided by twisting a rod having a parallelogram cross section is apparent from FIG. 4. In this respect, the spiral edges 18, 20, 22 and 24 are arranged in two pairs. The first pair is formed by edges 20 and 24 and the second pair is formed by a parallelogram edges 18 and 22. One pair 20, 24 extends along the ends of the major diameter 26 of the twisted blank and one pair 18, 22 extends along the end of the minor diameter 28 of the twisted blank. These major and minor diameters correspond generally to the long and short diagonals respectively of the parallelogram cross section. The major and minor diameters alternate with the number of diameters being dependent upon the length of the instrument and the number of times that the blank is twisted. In any event, the spiral edges 20, 24 defining the larger diameter sections provide the cutting edges whereas the second set of alternating edges 18, 22 defining the reduced diameter sections provide a retaining and debris removal function during operation of the instrument.

It has been found that an endodontic instrument in accordance with the present invention has a strength which meets specifications of the American Dental Association. While these instruments do not have the strength of comparable K-files (i.e. a square cross section) instruments of the present invention (i.e. parallelogram cross section) do have better twist strength and stiffness than comparable sized reamers (triangular cross section) or Hedstrom files.

Tests for the strength of endodontic instruments are fairly standardized and includes tests for both twist strength and stiffness. Briefly, the procedure for determining twist strength involves holding in a fixed position, the handle end of the instrument while the pointed or working end is rotated axially in a direction opposite to the normal twist of the instrument. For example, in endodontic instruments having a counter clockwise twist or spiral, the test would be conducted by rotating the pointed or working end clockwise.

Rotation continues until the instrument breaks. Both the torque (gm-cm) and angular deflection in degrees at the breaking point are taken as a measure of the twist strength of the instrument.

Stiffness of the instrument is tested by holding the instrument fixed by its pointed or working end. A side ways force is then exerted to bend the instrument about the fixed end. The torque needed to bend the instrument 45° and 90° is a measure of its stiffness.

Table I below compares both the twist strength and stiffness of an instrument of the present invention and in particular one with a rhombus cross section to a comparable sized K-file (square cross section) reamer (triangular cross section) and Hedstrom file (circular cross section).

TABLE I

|  | Rhombus | Hedstrom | K-File | Reamer |
|---|---|---|---|---|
| Twist Strength |  |  |  |  |
| Torque (gm-cm) | 59.7 | 43.3 | 75.9 | 50.2 |
| Angular Deflection | 895.1° | 438.1° | 686.4° | 848.8° |
| Stiffness |  |  |  |  |
| Torque at 45° | 65.4 | 40.8 | 102.2 | 44.9 |
| Torque at 90° | 68.6 | 43.4 | 104.5 | 46.8 |

The Table I above shows that the endodontic instrument of the present invention has a twist strength which is higher than either the reamer or Hedstrom file and which is more flexible (less stiff) than the K-file.

There is no generally accepted standardized test to determine the cutting efficiency of endodontic instruments. Accordingly, a simple test was designed to obtain empirically, data to support the claim made hereinabove that the instrument of the present invention has superior cutting ability over the reamers and K-files of the prior art. In the test, a pre-cast curved canal was molded in a plastic block. Endodontists were asked to open these canals with each of three instruments, an instrument which unknown to the endodontist had a rhombic cross section according to the present invention, a standard K-file and a reamer both of comparable size to the rhombic cross section. Upon being asked to compare the cutting characteristics of each instrument twenty-eight of thirty endodontists making the comparison chose the rhombic shaped instrument as being far superior in cutting, material removal and flexiblity than either the K-file or reamer.

Thus, it should be appreciated that the present invention does provide a superior endodontic instrument which combines the favorable characteristics of each prior art instrument. In this respect, the instrument of the present invention is more flexible than a conventional K-file, has a greater twist strength than the conventional reamer or Hedstrom file and can be said to rank above either the K-file or reamer in cutting ability.

We claim:

1. In an Endodontic Instrument for use in root canal preparation including an axially tapered flexible rod for insertion into the root canal, said rod having spiral faces defining spiral edges between them and a handle portion fixed to the rod for manipulating the endodontic Instrument, the improvement comprising:
   said rod having a tetragonal cross section, the sides of which are substantially flat and define at least one obtuse angle and one acute angle, the spiral edge corresponding to each acute angle being a cutting edge.

2. An endodontic instrument as in claim 1 wherein said at least one obtuse angle is less than 120°.

3. An endodontic instrument as in claim 1 wherein said at least one acute angle is greater than 60°.

4. An endodontic instrument comprising:
   (a) a handle for manipulating the instrument;
   (b) a tapered file extending from said handle, said file in cross section being generally the shape of an oblique parallelogram having a major diagonal and a minor diagonal; and
   (c) said file being axially twisted over at least a portion of its length to provide two spiral cutting edges at the ends of said major diagonal which alternates with two spiral edges at the ends of said minor diagonal.

5. A method of making an endodontic instrument comprising the steps of:
   (a) grinding an elongaged tapered rod to provide a generally parallelogram cross section for at least a portion of its length, said parallelogram cross section having opposite obtuse angles, a major diagonal and a minor diagonal;
   (b) axially twisting said rod after grinding to provide four spiraling edges, two of said edges defining the major diagonal alternating with two of said edges defining said minor diagonal; and
   (c) fixing one end of said rod to a handle for manipulating said instrument.

6. A method as in claim 5 wherein said grinding step provides said rod with a rhomboid cross section.

7. A method as in claim 6 wherein said grinding step provides said rod with a rhombus cross section.

8. A method as in claim 6 wherein said grinding step provides said rod with two opposite obtuse angles of between about 105°–120° and two opposite acute angles of between about 60° and 75°.

9. An endodontic cutting instrument comprising:
   (a) an elongated, axially twisted tapered rod, said rod being sufficiently flexible to follow the root canal;
   (b) said rod in cross section being the shape of an oblique parallelogram with two obtuse angles and two acute angles; and
   (c) the edges of said rod corresponding to the acute angles of said oblique parallelogram cross sectional shape being the cutting edges of said instrument.

10. A endodontic instrument as in claim 9 wherein said parallelogram is a rhomboid.

11. An endodontic instrument as in claim 9 wherein said parallelogram is a rhombus.

12. An endodontic instrument as in claim 9 wherein said obtuse angles are about 105°–120°.

13. An endodontic instrument as in claim 9 wherein said blank is axially twisted about 8–20 full revolutions.

* * * * *